United States Patent [19]

Woltersdorf, Jr. et al.

[11] 4,454,148

[45] Jun. 12, 1984

[54] 5-HYDROXY-2-BENZOTHIAZOLESUL-FONAMIDE FOR THE TOPICAL TREATMENT OF ELEVATED INTRAOCULAR PRESSURE

[75] Inventors: Otto Woltersdorf, Jr., Chalfont; Harvey Schwam, Lafayette Hills; Stuart R. Michelson, Lansdale; John M. Sondey, Hatfield, all of Pa.

[73] Assignee: Merck & Co., Inc., Rahway, N.J.

[21] Appl. No.: 448,149

[22] Filed: Dec. 9, 1982

Related U.S. Application Data

[63] Continuation-in-part of Ser. No. 413,211, Sep. 2, 1982, abandoned.

[51] Int. Cl.³ .................. A61K 31/425; C07D 231/00
[52] U.S. Cl. ...................................... 424/270; 548/172
[58] Field of Search ........................ 424/270; 548/172

[56] References Cited

U.S. PATENT DOCUMENTS 3,630,200 12/1971 Higuchi .
3,811,444 5/1974 Heller et al. .
3,845,201 10/1974 Haddad .
3,867,519 2/1975 Michaels .
3,868,445 2/1975 Ryde et al. .
3,981,303 9/1976 Higuchi .
4,177,256 12/1979 Michaels et al. .
4,386,098 5/1983 Woltersdorf et al. .............. 424/270

OTHER PUBLICATIONS

Am. J. Vet. Res. 40 (3), 334-345 (1979)–Gelatt et al.
The Merck Index, 9th Ed., Item 41–Merck & Co.–Rahway, N.J.
J. Med. Chem. 13 (5), 1012-1013 (1970)–Akerfeldt.
Chem. Abstracts, vol. 52, 20211-20214.

*Primary Examiner*—Douglas W. Robinson
*Attorney, Agent, or Firm*—William H. Nicholson; Mario A. Monaco

[57] ABSTRACT

5-Hydroxy-2-benzothiazolesulfonamide is useful for the topical treatment of elevated intraocular pressure. Ophthalmic compositions including drops and inserts are disclosed.

8 Claims, No Drawings

5-HYDROXY-2-BENZOTHIAZOLESULFONAMIDE FOR THE TOPICAL TREATMENT OF ELEVATED INTRAOCULAR PRESSURE

RELATED APPLICATION

This application is a continuation-in-part of application Ser. No. 413,211 filed Sept. 2, 1982 abandoned.

SUMMARY OF THE INVENTION

This invention relates to 5-hydroxy-2-benzothiazolesulfonamide, found to be useful in the reduction of elevated intraocular pressure. More particularly this invention relates to compositions including the compound of the structural formula

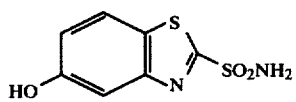

as well as the ophthalmologically acceptable salts thereof wherein the active entity is incorporated in a composition comprising the 5-hydroxy-2-benzothiazolesulfonamide or its salt, and a ophthalmologically suitable carrier therefor. This invention especially relates to methods for the treatment of elevated intraocular pressure, especially when accompanied by pathological damage such as in the disease known as glaucoma.

BACKGROUND OF THE INVENTION

Glaucoma is an ocular disorder associated with elevated ocular pressures which are too high for normal function and may result in irreversible loss of visual function. It untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure.

Although pilocarpine and physostigmine increase the outflow of aqueous humor and thus reduce intraocular pressure, they have no effect on the biological mechanism largely responsible for aqueous humor formation, the carbonic anhydrase pathway. Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of exposing body carbonic anhydrase to their action. Such a potential gross disruption of a basic enzyme system is justified only during an acute attack of alarmingly elevated intraocular pressure, or when no other agent is effective. Despite the desireability of directing the carbonic anhydrase inhibitor only to the desired ocular target tissue, no topically effective carbonic anhydrase inhibitors are presently available for clinical use.

DESCRIPTION OF THE INVENTION

Compositions of 5-hydroxy-2-benzothiazolesulfonamide or an ophthalmologically acceptable salt thereof are now found to inhibit carbonic anhydrase and, moreover, to lower intraocular pressure when topically administered to the mammalian eye, particularly in the form of drops or inserts. Examples of such ophthalmologically acceptable salts include the alkali metal salts.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose is satisfactory.

When administered for the treatment of elevated intraocular pressure or glaucoma, the active compound is most desireably administered topically to the eye, although systemic treatment is also satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation.

In such formulations, from 0.01% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

In the form of an ophthalmic solution, the active drug can be employed as ophthalmologically acceptable salts such as the sodium and potassium salts obtained by neutralizing an equivalent of the sulfonamide with an equivalent of a suitable base such as, for example, an alkali metal hydroxide.

The active drug of this invention is most suitably administered in the form of ophthalmic pharmaceutical compositions adapted for topical administration to the eye such as a suspension, ointment, or as a solid insert. Formulations of these compounds may contain from 0.01 to 15% by weight and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The thrust of this invention as hereinbefore stated is to provide an ocular antihypertensive agent for the eye, both human and animal, that acts by inhibiting carbonic anhydrase and, thereby, impeding the formation of aqueous humor.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, others may prefer a solid medicament that is topically applied to the eye, for example, a solid dosage form that is suitable for insertion into the cul-de-sac. To this end the carbonic anhydrase inhibiting agent can be included with a non-bioerodible insert, i.e. one which after dispensing the drug remains essentially intact, or a bioerodible insert, i.e. one that either is soluble in lacrimal fluids, or otherwise disintegrates. While the insert employed is not critical and those disclosed in U.S. Pat. No. 3,630,200 Higuchi; U.S. Pat. No. 3,811,444 Heller et al.; U.S. Pat. No. 4,177,256 Michaels et al.; U.S. Pat. No. 3,868,445 Ryde et al; U.S. Pat. No. 3,845,201 Haddad; U.S. Pat. No. 3,981,303 Higuchi; and U.S. Pat. No. 3,867,519 Michaels, are satisfactory; in general, however, the insert described below is found preferable.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropyl methyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert, is available in several polymeric forms, all of which are suitable in the preparation of these inserts. Thus, the product sold by Hercules, Inc. of Wilmington, Del., under the name KLUCEL such as KLUCEL HF, HWF, MF, GF, JF, LF and EF which are intended for food or pharmaceutical use, are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX, a polymer supplied by Union Carbide Co., may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and esecially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and, accordingly, the medicament in any desired length of time. The inserts, therefore, can be prepared to allow for retention and, accordingly, effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be prepared readily, for example, by dissolving the medicament and the polymer in a suitable solvent and the solution evaporated to afford a thin film of the medicated polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye. The insert can be of any suitable size which readily fits into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4×5-20 mm. or ovals of comparable size. Similarly, extruded rods having a diameter between about 0.5 and 1.5 mm. can be cut into suitable sections to provide the desired amount of medicated polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The medicated ocular inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from 0% up to about 30% by weight. A particularly preferred plasticizer is water which is present in amounts of at least about 5% up to 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 100 mg. of water soluble polymer, more particularly fom 5 to 50 mg. and especially from 5 to 20 mg. The medicament is present from about 0.1 to about 25% by weight of insert.

EXAMPLE 1

5-Hydroxy-2-benzothiazolesulfonamide

Step A

5-Methoxy-2-benzothiazolethiol

A mixture of 2-amino-4-methoxybenzenethiol (7.0 g, 0.045 mole), sodium hydroxide (4.4 g, 0.11 mole) and carbon disulfide (8.06 g, 0.11 mole) in 90% aqueous ethanol (100 ml.) was heated at reflux for 2 hours, filtered, diluted with ice-water and acidified with hydrochloric acid to give 7.0 g of 5-methoxy-2-benzothiazolethiol which melts at 192°-4° C. after recrystallization from benzene.

Analysis for $C_8H_7NOS_2$: Calculated: C, 48.71; H, 3.58; N, 7.10, Found: C, 49.13; H, 3.68; N, 7.31.

Step B

5-Methoxy-2-benzothiazolesulfonamide

To a stirred solution of conc. aqueous ammonia cooled to 0° C. was added simultaneously a solution of 5-methoxy-2-benzothiazolethiol (3.8 g, 0.019 mole) dissolved in sodium hydroxide (800 mg in 20 ml $H_2O$) and a solution of aqueous sodium hydrochloride (5.25%, 20 ml) over a ¼ hour period. The white sulfenamine which separated was filtered, washed with ice-$H_2O$ and transferred to a round bottom flask with acetone (50 ml.) and water (90 ml). The stirred suspension was treated over a 1 hour period with 5% aqueous $KMnO_4$ (88 ml). The resulting solution was filtered and acidified with HCl to give 3.7 g of 5-methoxy-2-benzothiazolesulonamide which melts at 186° C. after recrystallization from ethylene chloride.

Analysis for $C_8H_8N_2O_3S_2$: Calculated: C, 39.33; H, 3.30; N, 11.47, Found: C, 39.43; H, 3.36; N, 11.40.

Step C

5-Hydroxy-2-benzothiazolesulfonamide

A stirred suspension of 5-methoxy-2-benzothiazolesulfonamide (11.8 g, 0.048 mole) and aluminum chloride (28 g, 0.21 mole) in heptane (500 ml) was heated at reflux for 2¼ hours then cooled. The aluminum chloride complex was decomposed by the addition of ice water (400 ml) to give 6.5 g of 5-hydroxy-2-benzothiazolesulfonamide which melts at 224° C. after reprecipitiation from dilute sodium hydroxide with dilute hydrochloric acid.

Analysis for $C_7H_6N_2O_3S_2$: Calculated: C, 36.51; H, 2.63; N, 12.17; Found: C, 36.84; H, 2.64; N, 11.97.

The following examples of ophthalmic formulations are given by way of illustration.

EXAMPLE 2

Solution Composition

| | | |
|---|---|---|
| 5-Hydroxy-2-benzothiazole-sulfonamide (I) | 1 mg. | 15 mg. |
| Monobasic sodium phosphate.$2H_2O$ | 9.38 mg. | 6.10 mg. |
| Dibasic sodium phosphate.$12H_2O$ | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the solution is adjusted to 6.8 and the final solution diluted to volume. The solution is rendered sterile by filtration through a sterilizing filter.

EXAMPLE 3

| 5-Hydroxy-2-benzothiazole-<br>sulfonamide (I) | 5 mg. |
|---|---|
| petrolatum q.s. ad. | 1 gram |

Compound I and the petrolatum are aseptically combined.

EXAMPLE 4

| 2-Sulfamoyl-5-Benzothiazolyl<br>Butyrate | 1 mg. |
|---|---|
| Hydroxypropyl cellulose q.s. | 12 mg. |

Ophthalmic inserts are manufactured from compression molded films which are prepared on a Carver Press by subjecting the powdered mixture of the above ingredients to a compressional force of 12,000 lbs. (guage) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 5

| 5-Hydroxy-2-benzothiazole-<br>sulfonamide | 1 mg. |
|---|---|
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 6

| 5-Hydroxy-2-benzothiazole-<br>sulfonamide | 1 mg. |
|---|---|
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 7

| 5-Hydroxy-2-benzothiazole-<br>sulfonamide | 1 mg. |
|---|---|
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (guage) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

After packaging a convenient quality of inserts, usually a single dose, the package is exposed to a sterilizing quantity of radiation. The preferred packaging employs sealing the inserts between layers of film or foil and then sealing or laminating the layers together about the edges. The techniques for performing the sterilization are well known and accepted, for example, as outlined in International Atomic Energy Commission, *Code of Practice for Radiosterilization of Medical Products*, 1967, pp. 423–431; and Block, *Disinfection, Sterilization and Preservation*, 2nd Ed., Lea & Febiger, Philadelphia, 1977, pp. 542–561.

The required quantity of irradiation can be determined experimentally by testing irradiated inserts for viable bacteria. Generally, the amount of irradiation desired to achieve sterilization is defined by the $D_{10}$ value. The $D_{10}$ value is the radiation dose that will reduce a given population of organisms by a factor of 10. Based on $D_{10}$ values, experimentally obtained for *Bacillus pumilus*, and presterilization contamination levels, a dose of 1.36 megarads is effective in obtaining a sterile product.

Ophthalmic suspensions for treating elevated intraocular pressure in the mammalian, human and animal eye using an active drug of this invention can also be prepared by employing flocculating agents and deflocculating or suspending agents together, and by employing ratios of the various proportional amounts of medicament, vehicle, flocculating agent and deflocculating agent in the total suspension. Thus, the ophthalmic suspension can comprise from 1 to 15 mg/ml of total suspension of the medicament, deflocculating agent as hereinafter defined, and flocculating agent as hereinafter defined, provided that the ratio of flocculating agent to deflocculating agent is from 7:1 to 30:1, especially 10:1 to 15:1, respectively, and the ratio of medicament to deflocuulating agent is from 300:1 to 1:2, especially 60:1 to 1:1, respectively. In its preferred aspect, however, the opthalmic suspension composition of the present invention will contain from 1 to 15 mg/ml and especially 2.5 to 10 mg/ml of total suspension of medicament; 0.05 to 1.7 mg/ml and especially 0.15 to 1.5 mg/ml of total suspension of deflocculating agent; and 3 to 17 mg/ml and especially 4 to 15 mg/ml of total suspension of flocculating agent. The ophthalmic suspension compositions can also contain certain excipients whose presence is desirable in preparing an acceptable ophthalmic suspension. The nature and proportional amounts of these excipients will be discussed in detail hereinafter.

The flocculating agents employed are alkanols of 1 to 4 carbon atoms, and aromatic alcohols selected from the group consisting of benzyl alcohol, β-phenyl-ethyl alcohol and cinnamyl alcohol, and mixtures of the above. Mixtures of varying proportions are suitable, and, for example, a mixture of benzyl alcohol and β-phenylethyl alcohol in a ratio of approximately 1:1 by weight has been found to give excellent results. As indicated previously, the flocculating agent will be employed in the ophthalmic suspension in amounts such that the ratio of flocculating agent to deflocculating agent is from 7:1 to 30:1, especially 10:1 to 15:1, respectively.

The deflocculating or suspending agents employed in the ophthalmic suspension compositions are products derived from the condensation of polymers of ethylene oxide containing from 10 to 50 oxyethylene repeating units, and esters of fat acids of 10 to 18 carbon atoms. Especially suitable are such condensation products from fatty acid esters of sorbitol, particularly the lauric, stearic and oleic acid esters of sorbitol. The fatty acid esters may be employed as mixtures from naturally occurring oils, which are esters of fatty acids and glycerol. Thus, the deflocculating agent may be polyoxyethylene vegetable oil, available as Emulphor EL-719 from GAF Corporation. Naturally occurring fatty acid mixtures may be employed to produce esters of sorbitol for condensation with polyoxyethylene. Thus, the deflocculating agent may be polyoxyethylene sorbitol lanolin, polyoxyethylene sorbitol tallow esters, and polyoxyethylene sorbitol tall oil, available respectively, as Atlas G-1441, Atlas G-3284, and Atlox 1256 from Atlas Chemical Industries. Particularly preferred are esters of sorbitol and specific fat acids, especially lauric, stearic and oleic acids. Thus, the deflocculating agent may be polyoxyethylene sorbitan monolaurate, polyoxyethylene sorbitan monostearate, or polyoxyethylene sorbitan monoleate, available, respectively, as Atlas G-7569J, Tween 80 from Atlas Chemical Industries. The last named product, Tween 80, which contains 20 oxyethylene units, has been found to be especially suitable. As indicated previously, the deflocculating agent will be employed in the ophthalmic suspension in amounts such that the ratio of medicament to deflocculating agent is from 300:1 to 1:2, especially 60:1 to 1:1, respectively.

By use of the particular flocculating and deflocculating agents described above, and in the critical range of proportionate amount ratios of the present invention, it is possible to obtain acceptable ophthalmic suspension compositions for the active drug which have the highly desirable properties of having the suspended material uniformly dispersed therein during the period of administration to the eye of the patient, while at the same time facilitating easy redispersion of that material after its flocculation and separation in the ophthalmic suspension composition.

In addition to the medicament, flocculating and deflocculating agents and water, conventional excipients and other materials are advantageously employed in preparing the ophthalmic suspension compositions of the present invention in accordance with good pharmaceutical practice. For example, the ophthalmic suspensions are sterile and preferably contain a bacteriological preservative to maintain sterility during use. Quarternary ammonium bacteriostats such as benzalkonium chloride may be used as well as phenyl mercuric acetate, phenyl mercuric nitrate, thimerosal, benzyl alcohol, or β-phenylethyl alcohol. These bacteriostats may suitably be used in a range of from 0.01 to 3.0 mg/ml and preferably 0.1 to 0.2 mg/ml of total suspension. An antioxidant may also be used to prevent oxidation of the medicament. Suitable antioxidants include sodium bisulfate, N-acetyl cysteine salts, sodium ascorbate, sodium meta bisulfite, sodium acetone bisulfite and other acceptable antioxidants known to the pharmaceutical art. These antioxidants may suitably be used in a range of 0.1 to 10.0 mg/ml and preferably 0.2 to 3.5 mg/ml. In conjunction with the antioxidants, chelating agents such as disodium edetate may also be employed.

Viscosity inducing agents helpful in suspension characteristics of the composition, including cellulose derivatives such as hydroxymethyl cellulose, hydroxypropyl cellulose and methyl cellulose, may also be used in the formulation. For this purpose, one may use from 5.0 to 10.0 mg/ml and preferably from 1.5 to 3.5 mg/ml of such agents. Lecithin may also be used to produce helpful suspension characteristics for the ophthalmic suspension composition, being employed for this purpose in amounts of from 0.05 to 1.0 mg/ml of total suspension, and preferably from 0.1 to 0.4 mg/ml. A humectant is also sometimes used to help retain the water of the formulation in the eye. High molecular weight sugars are suitably used for this purpose such as sorbitol and dextrose in a concentration of from 0.1 to 10.0 mg/ml and especially 0.5 to 2.0 mg/ml. Finally, since the formulation is autoclaved to obtain initial sterility an autoclaving aid such as sodium chloride is normally added to the formulation. The ophthalmic suspension compositions of the present invention are prepared by methods well known in the pharmaceutical art. For example, Step (1): there is first prepared a supersaturated NaCl aqueous solution such that the volume of water does not exceed 2½ times the amount of NaCl, and excess NaCl remains undissolved. Step (2): The medicament is then dispersed in the saline solution of Step (1) until a wet paste is formed. Step (3): The paste is sterilized by autoclaving at 121° C. under 15 psig pressure. Step (4): The viscosity inducing agent which is employed is then dispersed in water, clarified, and sterilized by autoclaving. Step (5): The other components of the total suspension composition are then added to water to form a solution. Step (6): The medicament paste from Step (3) is then added aseptically to the viscosity inducing agent dispersion of step (4), and mixed. Step (7): The remaining suspension ingredients, prepared in Step (5), are added aseptically to the mixture from step (6) by way of sterilizing membrane. Step (8): Sufficient water is added to the suspension from Step (7) to give the total desired volume. Step (9): The suspension is then aseptically homogenized at 1500-2200 psig, subdivided and distributed to suitable sterile containers.

The following examples illustrate preparation of the improved ophthalmic suspension compositions of the present invention.

EXAMPLES 8-11

The following materials are admixed in a 1250 ml bottle: 24 g of 5-hydroxy-2-benzothiazolesulfonamide which is a sufficient amount of medicament to result in a concentration of 10 mg per ml in the final samples, allowing for previously established 3.0% average; 0.4 g sodium bisulfite, 12 g NaCl, and 28 ml water (at 180° F.). This mixture, (I), is autoclaved for 30 minutes at 121° C. under 15 psig. Separately, 3 g of hydroxyethylcellulose in 720 ml of water (II) and 0.4 g of lecithin in 80 ml of water (III) were autoclaved for 30 minutes at 121° C. Then, (III) is admixed with (I) for 2 hours, and the resultant mixture poured into (II). Another mixture (IV) is prepared from 20 g of sorbitol, 2.36 ml of benzalkonium chloride, 10 g of disodium edetate, and water to give a final solution volume of 900 ml. Then, (IV) is added to the mixture of (I), (II), and (III) in sufficient quantity to give 1.8 l. overall. The 1.8 l. mixture of I, II, III, and IV is then taken and homogenized using a homogenizer at 2000 psig. Stock solutions are then prepared for polyoxyethylene (20) sorbitan monooleate by dissolving 3 g of the material in 100 ml of water, and of benzyl alcohol/β-phenyl-ethyl alcohol by admixing 50 ml of each alcohol. Varying quantities of the two stock solutions are then added to four 90 ml aliquots of the homogenized mixture of (I), (II), (III), and (IV) prepared as described above, together with sufficient water to give a total of 100 ml for each of four different samples.

EXAMPLE 12

Solution Composition

| | |
|---|---|
| 5-Hydroxy-2-benzothiazole-sulfonamide | 0.1 mg. |
| Peanut oil q.s. ad. | 0.10 mg. |

The solution is rendered sterile by filtration through a sterilizing filter.

EXAMPLE 13

| | |
|---|---|
| 5-Hydroxy-2-benzothiazole-sulfonamide | 0.5 gm. |
| Petrolatum q.s. ad. | 1 gram | and the petrolatum are aseptically combined.

What is claimed is:

1. A method for treating elevated intraocular pressure which comprises topically applying to an affected eye an intraocular pressure lowering effective amount of a carbonic anhydrase inhibitor of the formula:

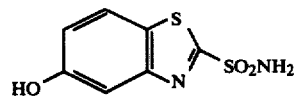

or an ophthalmologically acceptable salt thereof.

2. A method according to claim 1 wherein the carbonic anhydrase inhibitor is administered in a polymeric insert.
3. A method according to claim 2 where said insert comprises from 0.01 to 35% by weight of said 5-hydroxy-2-benzothiazolesulfonamide.
4. A method according to claim 2 wherein the polymer is hydroxypropylcellulose.
5. A method according to claim 1 wherein the compound is administered in an ointment base.
6. A method according to claim 1 wherein said compound is administered as a 0.01 to 5% by weight preparation of the compound in a liquid vehicle.
7. An ophthalmic composition for the topical treatment of glaucoma and ocular hypertension comprising an intraocular pressure lowering effective amount of a compound having the formula:

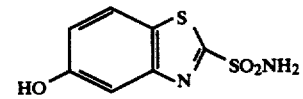

including pharmaceutically acceptable salts thereof and an ophthalmologically acceptable carrier.

8. The compound 5-hydroxy-2-benzothiazolesulfonamide or a pharmaceutically acceptable salt thereof.

* * * * *